United States Patent [19]

Keijsper et al.

[11] Patent Number: 5,171,832
[45] Date of Patent: Dec. 15, 1992

[54] POLYMERIZATION OF CARBON MONOXIDE/OLEFIN WITH P BIDENTATE LIGAND HAVING (1) ALKOXY PHENYL P GROUP AND (2) MONOSUBSTITUTED DIVALENT BRIDGING GROUP

[75] Inventors: Johannes J. Keijsper; Alexander W. van der Made, both of Amsterdam, Netherlands

[73] Assignee: Shell Oil Company, Houston, Tex.

[21] Appl. No.: 684,109

[22] Filed: Apr. 12, 1991

[30] Foreign Application Priority Data

Apr. 27, 1990 [NL] Netherlands ............... 9001019

[51] Int. Cl.$^5$ ................................ C08G 67/02
[52] U.S. Cl. ........................ 528/392; 502/162
[58] Field of Search ........................ 528/392

[56] References Cited

U.S. PATENT DOCUMENTS

| | | | |
|---|---|---|---|
| 3,694,412 | 9/1972 | Nozaki | 260/63 |
| 4,397,787 | 8/1983 | Riley | 260/429 R |
| 4,818,810 | 4/1989 | Drent | 528/392 |
| 4,835,250 | 5/1989 | Drent | 528/392 |
| 4,843,144 | 6/1989 | Van Broekhoven et al. | 528/392 |
| 4,868,282 | 9/1989 | Van Broekhoven et al. | 528/392 |
| 4,877,861 | 10/1989 | Van Doorn et al. | 528/392 |
| 4,880,903 | 11/1989 | Van Broekhoven et al. | 528/392 |
| 4,933,311 | 6/1990 | Van Doorn et al. | 502/162 |

FOREIGN PATENT DOCUMENTS

| | | |
|---|---|---|
| 121965 | 10/1984 | European Pat. Off. . |
| 181014 | 5/1986 | European Pat. Off. . |
| 213671 | 3/1987 | European Pat. Off. . |
| 257663 | 3/1988 | European Pat. Off. . |
| 296687 | 12/1988 | European Pat. Off. . |
| 320269 | 6/1989 | European Pat. Off. . |
| 379260 | 7/1990 | European Pat. Off. . |
| 380162 | 8/1990 | European Pat. Off. . |

*Primary Examiner*—Harold D. Anderson

[57] ABSTRACT

An improved process for the production of linear alternating polymers of carbon monoxide and at least one ethylenically unsaturated hydrocarbon employs a novel catalyst composition formed from a compound of palladium, the anion of a strong non-hydrohalogenic acid and a bidentate ligand of phosphorus wherein each monovalent phosphorus substituent is phenyl substituted by at least one alkoxy group on a ring carbon atom ortho to the atom through which the group is connected to phosphorus and the divalent alkylene bridging group has a single substituent (other than hydrogen) having atoms of carbon, hydrogen and optionally oxygen.

13 Claims, No Drawings

POLYMERIZATION OF CARBON MONOXIDE/OLEFIN WITH P BIDENTATE LIGAND HAVING (1) ALKOXY PHENYL P GROUP AND (2) MONOSUBSTITUTED DIVALENT BRIDGING GROUP

FIELD OF THE INVENTION

This invention relates to an improved process for the production of linear alternating polymers of carbon monoxide and at least one ethylenically unsaturated hydrocarbon. More particularly, the invention relates to such a polymerization process employing a catalyst composition formed from, inter alia, a bidentate phosphorus ligand incorporating a monosubstituted alkylene linking group between the two phosphorus atoms.

BACKGROUND OF THE INVENTION

The class of linear alternating polymers of carbon monoxide and at least one ethylenically unsaturated hydrocarbon has been known for some time. Such polymers were produced by Nozaki, e.g., U.S. Pat. No. 3,694,412, using arylphosphine complexes of palladium moieties as catalysts and certain inert solvents. More recent methods for the production of such linear alternating polymers, now known as polyketone polymers or polyketones, are illustrated by a number of published European Patent Applications including Nos. 121,965, 181,014, 213,671 and 257,663. The processes generally involve the use of a catalyst composition formed from a compound of palladium, cobalt or nickel, the anion of a strong non-hydrohalogenic acid and a bidentate ligand of phosphorus, arsenic, antimony or nitrogen.

The polyketone polymers are relatively high molecular weight materials having established utility as premium thermoplastics. The polyketone polymers are processed by techniques conventional for thermoplastics, e.g., injection molding, extrusion or thermoforming, into shaped articles of established utility.

Although the scope of the polymerization to produce polyketone polymers is extensive, a preferred catalyst composition is formed from a compound of palladium, the anion of a non-hydrohalogenic acid having a pKa below 2 and a bidentate ligand of phosphorus. Although each of the catalyst composition components has a considerable influence on the activity of the catalyst formed as well as upon the properties of the polymer produced by the polymerization process employing such a catalyst composition, the nature of the bidentate phosphorus ligand appears to be particularly important. Among the preferred bidentate phosphorus ligands of early processes were bis(hydrocarbyl aryl)phosphinoalkanes such as 1,3-bis(diphenylphosphino)propane. Somewhat later, it was found that better results were obtained when each monovalent phosphorus substituent contained a polar group, particularly an alkoxy group such as methoxy. Particularly useful were bidentate phosphine ligands wherein each monovalent phosphorus substituent was phenyl with an alkoxy substituent on an aromatic ring carbon atom ortho to the carbon atom through which the substituent is connected to the phosphorus. An example of a particularly preferred bidentate ligand of this type is 1,3-bis[di(2-methoxyphenyl)phosphino]propane. Such substituted-phenyl diphosphines, although providing catalyst compositions which result in faster reaction rates and higher molecular weight product, are somewhat more difficult to prepare.

In published European Patent Application 296,687 there is described a class of bidentate ligands wherein the divalent aliphatic linking group joining the two phosphorus atoms is alkylene disubstituted with alkyl or other substituents. Illustrative of such ligands are 2,2-dimethyl-1,3-bis(diphenylphosphino)propane and 2,2-dimethyl-1,3-bis[di(2-methoxyphenyl)phosphino]propane. The presence of disubstitution in the alkylene linking group provides catalyst compositions which give good results regardless of whether the monovalent phosphorus substituents are hydrocarbyl or polar-substituted hydrocarbyl. It would be of advantage, however, to provide additional bidentate ligands of phosphorus, the use of which results in catalyst compositions which afford polyketone polymers at higher polymerization rates and with higher molecular weight polymer.

SUMMARY OF THE INVENTION

The present invention provides an improved process for the production of linear alternating polymers of carbon monoxide and at least one ethylenically unsaturated hydrocarbon. More particularly, the invention provides a process of polymerizing carbon monoxide and at least one ethylenically unsaturated hydrocarbon in the presence of a catalyst composition formed from a compound of palladium, the anion of a strong non-hydrohalogenic acid and certain bidentate ligands of phosphorus in which the alkylene group linking the phosphorus atoms has one substituent group having atoms of carbon, hydrogen and optionally oxygen. The invention also provides that catalyst composition.

DESCRIPTION OF THE INVENTION

The present invention comprises a process including a catalyst composition for the production of linear alternating polymers of carbon monoxide and at least one ethylenically unsaturated hydrocarbon by contacting the carbon monoxide and hydrocarbon under polymerization conditions in the presence of a reaction diluent and a catalytic quantity of a catalyst composition formed from a compound of palladium, the anion of a strong non-hydrohalogenic acid and a bidentate ligand of phosphorus in which each monovalent substituent of phosphorus is a 2-alkoxyphenyl group and a monosubstituted alkylene group links the two phosphorus atoms.

The ethylenically unsaturated hydrocarbons which serve as precursors of the linear alternating polymers have up to 20 carbon atoms inclusive, preferably up to 10 carbon atoms inclusive, and are aliphatic including ethylene and other α-olefins such as butylene, isobutylene, 1-hexene, 1-octene and 1-dodecene, or are arylaliphatic containing a single aromatic substituent on an otherwise aliphatic molecule, particularly an aryl substituent on a carbon atom of the ethylenic unsaturation. Illustrative of this latter class of ethylenically unsaturated hydrocarbons are styrene, p-methylstyrene, p-ethylstyrene and m-isopropylstyrene. The preferred polyketone polymers are copolymers of carbon monoxide and ethylene or terpolymers of carbon monoxide, ethylene and a second hydrocarbon of at least 3 carbon atoms, particularly an α-olefin such as propylene.

When the preferred terpolymers are produced by the process of the invention, there will be at least about 2 units incorporating a moiety of ethylene for each unit employing a moiety of the second hydrocarbon. Preferably, there will be from about 10 units to about 100 units incorporating a moiety of ethylene for each unit incorporating a moiety of the second hydrocarbon. The polymer chain of the preferred polymers are therefore represented by the repeating formula

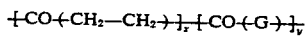

wherein G represents the moiety of an ethylenically unsaturated hydrocarbon of at least 3 carbon atoms polymerized through the ethylenic unsaturation thereof and the ratio of y:x is no more than about 0.5. When the preferred copolymers of carbon monoxide and ethylene are produced there will be no second hydrocarbon present and the copolymers are represented by the above formula I wherein y is zero. When y is other than zero, i.e., terpolymers are produced, the —CO—(—CH$_2$—CH$_2$—) units and the —CO—(—G—) units are found randomly throughout the polymer chain and the ratio of y:x is from about 0.01 to about 0.1. The end groups or "caps" of the polymer chain will depend upon what materials are present during polymerization and whether and how the polymer was purified. The particular nature of the end groups is of little significance insofar as the overall properties of the polymer are concerned so that the polymer is fairly represented by the formula for the polymer chain as depicted above.

Of particular interest are the polymers of number average molecular weight from about 1000 to about 200,000, particularly those polymers of number average molecular weight from about 20,000 to about 90,000, as determined by gel permeation chromatography. Such polymers will typically have a melting point from about 175° C. to about 300° C. but more often from about 210° C. to about 270° C. The polymers will generally have a limiting viscosity number (LVN), measured in a standard capillary viscosity measuring device, of from about 0.4 dl/g to about 10 dl/g, preferably from about 0.8 dl/g to about 4 dl/g.

The polymers are produced by the general procedures illustrated by the above published European Patent Applications. The carbon monoxide and the hydrocarbon monomers are contacted under polymerization conditions in the presence of a reaction diluent and a catalytic amount of the catalyst composition of the invention formed from a compound of palladium, the anion of a strong non-hydrohalogenic acid and the particular bidentate ligands of phosphorus of the invention.

The compound of palladium is preferably a palladium carboxylate, particularly a palladium alkanoate, and palladium acetate, palladium propionate, palladium butyrate and palladium hexanoate are satisfactory. Palladium acetate is particularly preferred. The anion is preferably an anion of a non-hydrohalogenic acid having a pKa below 2. Illustrative of acids whose anions are suitable precursors of the catalyst composition are inorganic acids such as sulfuric acid or perchloric acid or organic acids including carboxylic acids such as trichloroacetic acid, trifluoroacetic acid, dichloroacetic acid and difluoroacetic acid, as well as sulfonic acids such as methanesulfonic acid, trichloromethanesulfonic acid and p-toluenesulfonic acid. Particularly preferred are trifluoroacetic acid and p-toluenesulfonic acid. The anion is preferably provided as the free acid but alternatively the anion is provided as a metal salt, particularly a non-noble transition metal salt. However provided, the quantity of anion to be employed is from about 1 mole to about 100 moles per mole of palladium, preferably from about 2 moles to about 50 moles per mole of palladium.

The bidentate ligand of phosphorus to be employed in the catalyst compositions of the invention contain monovalent phosphorus substituents which are phenyl substituted by one or more alkoxy substituents at least one of which is located on a ring carbon atom which is ortho to the carbon atom through which the substituent is attached to phosphorus and contain a divalent alkylene linking group containing one substituent having atoms of carbon, hydrogen and optionally oxygen. Such bidentate phosphine substituents are represented by the formula

wherein R independently is phenyl substituted with at least one alkoxy substituent at least one of which is on a ring carbon atom ortho to the ring carbon atom through which the R group is connected to the phosphorus and R' is a divalent alkylene group substituted with one substituent having only atoms of carbon, hydrogen and optionally oxygen. Illustrative R groups include 2-methoxy, 2-ethoxy, 2,6-dimethoxy, 2-methoxy-4-ethoxy and 2,6-diethoxy-4-methoxy. The R' group preferably has up to 15 carbon atoms inclusive and from 2 to 4 carbon atoms inclusive in the bridge between the phosphorus atoms but monosubstituted three-carbon R' groups are particularly preferred. The single substituent on the R' group (other than hydrogen) is alkyl such as ethyl or hexyl, aralkyl such as benzyl or p-methylbenzyl, aryl such as phenyl or naphthyl, alkaryl such as tolyl or xylyl, alkaryloxy such as benzyloxy or 2,4,6-trimethylbenzyloxy, alkoxyalkoxy such as ethoxymethoxy or 2-(propoxy)ethoxy or hydroxyalkyl such as 6-hydroxyhexyl or 4-hydroxyoctyl. Preferred R' groups are further represented in the formula

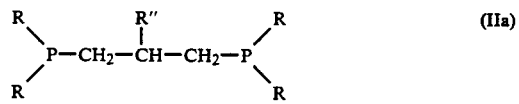

wherein R" is alkyl, aryl, alkaryl, aralkyl, aralkyloxy, alkoxyalkoxy or hydroxyalkyl and R has the previously stated meaning. The class of bidentate phosphine ligands of the above formula II wherein each R is 2-methoxyphenyl is a preferred class of ligands. Illustrative of such ligands are 2-phenyl-1,3-bis[di(2-methoxyphenyl)phosphino]propane, 2-bensyl-1,3-bis[di(2-methoxyphenyl)phosphino]propane, 2-propyl-1,3-bis[di(2-methoxyphenyl)phosphino]propane, 2-benzyloxy-1,3-bis[di(2-methoxyphenyl)-phosphino]propane, 2-(ethoxymethoxy)-1,3-bis[di(2-methoxyphenyl)phosphino]-propane and 2-(2,4,6-trimethylbenzyloxy)-1,3-bis[di(2-methoxyphenyl)phosphino]propane.

The bisdiphosphino substituted propanes of the above formula IIa are, in many instances, novel compounds but are produced by known methods. The preferred method is by reacting the appropriately substituted 1,3-dibromopropane with di(2-methoxyphenyl)phosphide in liquid ammonia. For example, 2-phenyl-1,3-dibromopropane reacts with di(2-methoxyphenyl)-phosphide in liquid ammonia to produce 2-phenyl-1,3- bis[di(2-methoxyphenyl)-phosphino]propane. The 1,3-dibromopropane reactants are also produced by known methods. The 2-hydrocarbyl-1,3-dibromopropane compounds are illustratively produced by alkylating or arylating diethylmalonate followed by reduction of the diester to the dialcohol as with lithium aluminum hydride and conversion to the dibromide by reaction with hydrobromic acid. The alkoxy-substituted 1,3-dibromopropane compounds are illustratively produced by reaction of an alkyl bromide with epibromohydrin.

The bidentate phosphine ligand is employed in the formation of the catalyst composition of the invention in an amount from about 0.5 mole to about 2 moles per mole of palladium. Preferred quantities of bidentate phosphine ligand are from about 0.75 mole to about 1.5 mole per mole of palladium.

The carbon monoxide and hydrocarbon are contacted under polymerization conditions in a suitable reactor in the presence of a reaction diluent and the catalyst composition. Suitable molar ratios of carbon monoxide to total ethylenically unsaturated hydrocarbon are from about 10:1 to about 1:10. Preferred molar ratios of carbon monoxide to total unsaturated hydrocarbon are from about 5:1 to about 1:5. Useful reaction diluents include the lower alkanols such as methanol or ethanol and the lower alkanones such as acetone or methyl ethyl ketone. Methanol is preferred as reaction diluent. The catalyst is employed in an amount sufficient to provide from about $1 \times 10^{-7}$ mole to about $1 \times 10^{-3}$ mole of palladium per mole of total unsaturated hydrocarbon, preferably from about $1 \times 10^{-6}$ mole to about $1 \times 10^{-3}$ mole of palladium per mole of total ethylenically unsaturated hydrocarbon. Typical polymerization conditions include a reaction temperature from about 20° C. to about 150° C., more often from about 30° C. to about 130° C. Suitable reaction pressures are from about 2 bar to about 150 bar, but pressures from about 5 bar to about 100 bar are more frequently encountered.

Reactant contact during polymerization is facilitated by some means of agitation such as shaking or stirring. Subsequent to polymerization the reaction is terminated as by cooling the reactor and contents and releasing the pressure. The polymer product is typically obtained as a suspension in the reaction diluent. The polymer is recovered by conventional techniques such as filtration or centrifugation and is used as recovered or is purified as by contact with a solvent or complexing agent selective for catalyst residues.

The process of the invention is characterized by relatively high polymerization rates and the production of linear alternating polymer of relatively high molecular weight. These advantages are realized through the use of tetra(alkoxyphenyl) bidentate ligands incorporating a single substituent on the alkylene bridge connecting the phosphorus atoms. The improvement in catalytic activity appears to be specific for the alkoxyphenyl bidentate phosphorus ligands since similar substitution on a tetra(phenyl) bidentate ligand does not result in improved catalytic activity.

The polyketone product of the process of the invention is a thermoplastic material of established utility. The polymer is processed by procedures conventional for thermoplastics into a wide variety of shaped objects. Specific applications include the production of containers for food and drink and the production of parts and housings for automotive applications.

The invention is further illustrated by the following Comparative Examples (not of the invention) and the Illustrative Embodiments which should not be regarded as limiting. In the Comparative Examples and Illustrative Embodiments all carbon monoxide/ethylene/propylene terpolymers produced were linear alternating polymers and all limiting viscosity numbers were determined in m-cresol at 60° C.

COMPARATIVE EXAMPLE I

A terpolymer of carbon monoxide, ethylene and propylene was prepared by charging to an autoclave of 300 ml capacity equipped with a mechanical stirrer 135 ml of methanol, 4 ml of acetone, 0.009 mmol of palladium acetate, 0.19 mmol of trifluoroacetic acid and 0.01 mmol of 1,3-bis(diphenylphosphino)propane. The air in the autoclave was removed by three times pressurizing the autoclave to 50 bar with carbon monoxide and then releasing the pressure. The autoclave and contents were then heated to 80° C. and carbon monoxide was introduced to give a pressure of 25 bar, propylene was added until a pressure of 35 bar was reached and then ethylene until a total pressure of 50 bar was reached. During the polymerization which followed the pressure was maintained at 52 bar by addition of an equimolar mixture of carbon monoxide and ethylene. After 3.1 hours, the reactor and contents were cooled to ambient temperature and the pressure was released. The terpolymer was recovered by filtration, washed with methanol and dried. The yield of terpolymer was 13.0 g, obtained at a rate of 4.4 kg of terpolymer/g Pd hr. The terpolymer had an LVN of 0.5 dl/g.

COMPARATIVE EXAMPLE II

A carbon monoxide/ethylene/propylene terpolymer was prepared by a procedure substantially similar to that of Comparative Example I except that the catalyst composition solution contained 0.01 mmol of 2-benzyloxy-1,3-bis(diphenylphosphino)propane instead of 1,3-bis(diphenylphosphino)propane, the reaction temperature was 85° C. instead of 80° C. and the reaction time was 2.7 hours instead of 3.1 hours. The yield of terpolymer was 7.6 g, produced at the rate of 3.0 kg of polymer/g Pd hr. The terpolymer had an LVN of 0.3 dl/g.

COMPARATIVE EXAMPLE III

A carbon monoxide/ethylene/propylene terpolymer was produced by a procedure substantially similar to that of Comparative Example I except that the catalyst composition solution contained 0.01 mmol of 1,3-bis[di(2-methoxyphenyl)phosphino]propane instead of 1,3-bis(diphenylphosphino)propane, the reaction temperature was 85° C. instead of 80° C. and the reaction time was 2.9 hours instead of 3.1 hours. The yield of terpolymer was 13.1 g produced at the rate of 4.6 kg of polymer/g Pd hr. The terpolymer had an LVN of 1.1 dl/g.

ILLUSTRATIVE EMBODIMENT I

The compound 2-benzyl-1,3-dibromopropane was produced by adding 10 g (0.06 mmol) of 2-benzyl-1,3-dihydroxypropane to a mixture of 25 g of a 48% aqueous solution of hydrobromic acid and 7.5 g of concentrated sulfuric acid. After 6 g of concentrated sulfuric acid had been added, the mixture was boiled under reflux for 3.5 hours. After cooling and adding water, the mixture was extracted three times with dichloromethane. The organic layer was washed with water, 5% aqueous sodium bicarbonate and then again with water. The organic layer was then dried above magnesium sulfate and distilled. The yield of 2-benzyl-1,3-dibromopropane was 12 g, 68%.

ILLUSTRATIVE EMBODIMENT II

The compound 2-phenyl-1,3-dibromopropane was prepared by adding 0.13 mmol of phosphorus tribromide to a stirred mixture of 0.1 g pyridine and 0.065 mol of 2-phenyl-1,3-dihydroxypropane. The mixture was stirred at ambient temperature for 5 days and then heated at 100° C. for 2 hours. The mixture was then poured onto ice and extracted with dichloromethane. The organic layer was washed with water, 5% aqueous sodium bicarbonate, again with water and then dried over magnesium sulfate and distilled. The yield of 2-phenyl-1,3-dibromopropane was 71%.

ILLUSTRATIVE EMBODIMENT III

The compound 2-propyl-1,3-dibromopropane was prepared by a procedure analogous to that of Illustrative Embodiment I except that 2-propyl-1,3-dihydroxypropane was used instead of 2-benzyl-1,3-dihydroxypropane. The yield of 2-propyl-1,3-dibromopropane was 62%.

ILLUSTRATIVE EMBODIMENT IV

The compound 2-benzyloxy-1,3-dibromopropane was produced by heating at 160° C. for 8 hours a mixture of 24.6 g (0.18 mmol) epibromohydrin, 29 g (0.17 mmol) benzyl bromide and 20 g of mercuric chloride. The resulting mixture was distilled under reduced pressure to give a yield of 2-benzyloxy-1,3-dibromopropane of 57%.

ILLUSTRATIVE EMBODIMENT V

The compound 2-(ethoxymethoxy)-1,3-dibromopropane was prepared by slowly adding 0.1 mol of freshly distilled ethyl chloromethyl ether to an ice-cooled mixture of 0.1 mol epichlorohydrin and 10 mg of mercuric chloride. After standing at ambient temperature for 12 hours the mixture was distilled to give a 96% yield of 2-(ethoxymethoxy)-1,3-dibromopropane.

ILLUSTRATIVE EMBODIMENT VI

The compound 2-(2,4,6-trimethylbenzyloxy)-1,3-dibromopropane was produced by a procedure analogous to that of Illustrative Embodiment V except that 1-bromomethyl-2,4,6-trimethylbenzene was used instead of the benzyl bromide. The yield of 2-(2,4,6-trimethylbenzyloxy)-1,3-dibromopropane was 90%.

ILLUSTRATIVE EMBODIMENT VII

The compound 2-benzyl-1,3-bis[di(2-methoxyphenyl)phosphino]propane was produced by a series of process steps conducted under argon. To 125 ml of dry ammonia at −78° C. were added 0.4 g (17.5 mmol) sodium, 3.1 g (8.75 mmol) tris(2-methoxyphosphine) and 12.5 ml of tetrahydrofuran which had been dried over sodium. After the ammonia was removed by evaporation, the tetrahydrofuran was removed by distillation at reduced pressure. The remaining solid was dissolved in 50 ml dichloromethane and washed with 50 ml of 5% aqueous ammonium chloride, after which the volume of solvent was reduced and 50 ml of tetrahydrofuran was added. The solution was filtered and concentrated and 50 ml of methanol were added to precipitate 2.53 g of 2-benzyl-1,3-bis[di(2-methoxyphenyl)phoshino]propane, a 95% yield.

ILLUSTRATIVE EMBODIMENT VIII

The compound 2-phenyl-1,3-bis[di(2-methoxyphenyl)phosphino]propane was prepared by a procedure substantially similar to that of Illustrative Embodiment VII except that 2-phenyl-1,3-dibromopropane was used instead of 2-benzyl-1,3-dibromopropane. The yield of 2-phenyl-1,3-bis[di(2-methoxyphenyl)phosphino]propane was 90%.

ILLUSTRATIVE EMBODIMENT IX

The compound 2-propyl-1,3-bis[di(2-methoxyphenyl)phosphino]propane was produced by a method substantially similar to that of Illustrative Embodiment VII except that 2-propyl-1,3-dibromopropane was used instead of 2-benzyl-1,3-dibromopropane. The yield of 2-phenyl-1,3-bis[di(2-methoxyphenyl)phosphino]propane was 90%.

ILLUSTRATIVE EMBODIMENT X

The compound 2-benzyloxy-1,3-bis[di(2-methoxyphenyl)phosphino]propane was produced by a procedure substantially similar to that of Illustrative Embodiment VII except that 2-benzyloxy-1,3-dibromopropane was used instead of 2-benzyl-1,3-dibromopropane. The yield of 2-benzyloxy-1,3-bis[di(2-methoxyphenyl)phosphino]propane was 91%.

ILLUSTRATIVE EMBODIMENT XI

The compound 2-(ethoxymethoxy)-1,3-bis[di(2-methoxyphenyl)phosphino]propane was produced by a procedure substantially similar to that of Illustrative Embodiment VII except that 2-(ethoxymethoxy)-1,3-dibromopropane was used instead of 2-benzyl-1,3-dibromopropane. The yield of 2-(ethoxymethoxy)-1,3-bis[di(2-methoxyphenyl)phosphino]propane was 20%.

ILLUSTRATIVE EMBODIMENT XII

The compound 2-(2,4,6-trimethylbenzoxy)-1,3-bis[di(2-methoxyphenyl)phosphino]propane was produced by a procedure substantially similar to that of Illustrative Embodiment VII except that 2-(2,4,6-trimethylbenzyloxy)-1,3-dibromopropane was used instead of 2-benzyl-1,3-dibromopropane. The yield of 2-(2,4,6-trimethylbenzyloxy)-1,3-bis[di(2-methoxyphenyl)phosphino]propane was 60%.

ILLUSTRATIVE EMBODIMENT XIII

A terpolymer of carbon monoxide, ethylene and propylene was produced by a procedure substantially similar to that of Comparative Example I except that 2-(2,4,6-trimethylbenzyloxy)-1,3-bis[di(2-methoxyphenyl)phosphino]propane was used instead of 1,3-bis(diphenylphosphino)propane, the reaction temperature was 85° C. instead of 80° C. and the reaction time was 3.4 hours instead of 3.1 hours. The yield of terpolymer was 16.6 g, produced at the rate of 5.4 kg of terpolymer/g Pd hr. The polymer had an LVN of 2.2 dl/g.

ILLUSTRATIVE EMBODIMENT XIV

A terpolymer of carbon monoxide, ethylene and propylene was produced by a procedure substantially similar to that of Comparative Example I except that 0.01 mmol of 2-benzyl-1,3-bis[di(2-methoxyphenyl)phosphino]propane was used instead of 1,3-bis(diphenylphosphino]propane, the reaction temperature was 85° C. instead of 80° C. and the reaction time was 3.4 hours instead of 3.1 hours. The yield of terpolymer was 19.5 g, produced at a rate of 6.0 kg of terpolymer/g Pd hr. The polymer had an LVN of 1.8 dl/g.

ILLUSTRATIVE EMBODIMENT XV

A carbon monoxide/ethylene/propylene terpolymer was prepared by a procedure substantially similar to that of Comparative Example I except that 0.01 mmol of 2-benzyloxy-1,3-bis[di(2-methoxyphenyl)phosphino]propane, was used instead of 1,3-bis(diphenylphosphino)propane, the reaction temperature was 85° C. instead of 80° C. and the reaction time was 2.5 hours instead of 3.1 hours. The yield of terpolymer was 20.8 g, produced at the rate of 8.7 kg of polymer/g Pd hr. The polymer had an LVN of 1.4 dl/g.

ILLUSTRATIVE EMBODIMENT XVI

A carbon monoxide/ethylene/propylene terpolymer was produced by a procedure substantially similar to that of Comparative Example I except that 0.01 mmol of 2-propyl-1,3-bis[di(2-methoxyphenyl)phosphino]propane was used instead of 1,3-bis(diphenylphosphino)propane, the reaction temperature was 85° C. instead of 80° C. and the reaction time was 2.2 hours instead of 3.1 hours. The yield of terpolymer was 12.5 g, produced at the rate of 5.8 kg of polymer/g Pd hr. The polymer had an LVN of 1.8 dl/g.

ILLUSTRATIVE EMBODIMENT XVII

A terpolymer of carbon monoxide, ethylene and propylene was produced by a procedure substantially similar to that of Comparative Example I except that the catalyst solution contained 135 ml methanol, 2 ml acetone, 0.0045 mmol palladium acetate, 0.09 mmol trifluoroacetic acid and 0.005 mmol 2-(6-hydroxyhexyl)-1,3-bis[di(2-methoxyphenyl)phosphino]-2-propane, the reaction temperature was 85° C. instead of 80° C. and the reaction time was 5.7 hours instead of 3.1 hours. The yield of terpolymer was 24.5 g, produced at the rate of 9.0 kg of polymer/g Pd hr. The polymer had an LVN of 2.4 dl/g.

What is claimed is:

1. In the process of producing a linear alternating polymer of carbon monoxide and at least one ethylenically unsaturated hydrocarbon by contacting the carbon monoxide and hydrocarbon under polymerization conditions in the presence of a reaction diluent and a catalyst composition formed from a compound of palladium, the anion of a strong non-hydrohalogenic acid and a bidentate ligand of phosphorus, the improvement wherein the ligand is a bidentate ligand represented by the formula

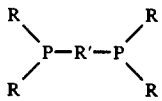

wherein R independently is phenyl substituted with at least one alkoxy substituent at least one of which is located on a phenyl ring carbon atom ortho to the phenyl ring carbon atom through which the R group is connected to phosphorus and R' is a divalent alkylene group of up to 15 atoms inclusive, and from 2 to 4 carbom atoms inclusive in the bridge between the phosphorus atoms, containing as a single substituent, other than hydrogen, a substituent having atoms of carbon and hydrogen with or without oxygen.

2. The process of claim 1 wherein the bidentate ligand is represented by the formula

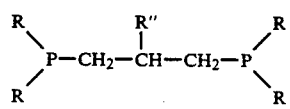

wherein R independently is phenyl substituted with at least one alkoxy group at least one of which is substituted on a phenyl ring carbon atom ortho to the phenyl ring carbon atom through which the R group is connected to phosphorus and R" is alkyl, aryl, alkaryl, aralkyl, aralkyloxy, alkoyalkoxy or hydroxyalkyl.

3. The process of claim 1 wherein R is 2-alkoxyphenyl.

4. The process of claim 3 wherein R" is phenyl.

5. The process of claim 3 wherein R" is benzyl.

6. The process of claim 3 wherein R" is benzyloxy.

7. The process of claim 3 wherein R" is 2,4,6-trimethylbenzyloxy.

8. In the process of producing a linear alternating terpolymer of carbon monoxide, ethylene and propylene by contacting the carbon monoxide, ethylene and propylene under polymerization conditions in the presence of a methanol reaction diluent and a catalyst composition formed from palladium acetate, the anion of trifluoroacetic acid or p-toluenesulfonic acid and a bidentate ligand of phosphorus, the improvement wherein the bidentate ligand is of the formula

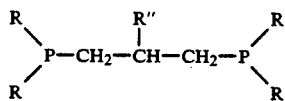

wherein R independently is 2-alkoxyphenyl and R" is alkyl, aryl, alkaryl, aralkyl, aralkyloxy, alkoxyalkoxy or hydroxyalkyl.

9. The process of claim 8 wherein R is 2-methoxyphenyl.

10. The process of claim 8 wherein R" is phenyl.

11. The process of claim 8 wherein R" is benzyl.

12. The process of claim 8 wherein R" is propyl.

13. The process of claim 8 wherein R" is 6-hydroxyhexyl.

* * * * *